(12) United States Patent
Dong (10) Patent No.: US 8,343,978 B2
(45) Date of Patent: Jan. 1, 2013

(54) FAST ONSET ORODISPERSABLE TABLETS

(75) Inventor: Liang Chang Dong, Sunnyvale, CA (US)

(73) Assignee: Adds Pharmaceuticals LLC, Oakland, CA (US)

( * ) Notice: Subject to any disclaimer, the term of this patent is extended or adjusted under 35 U.S.C. 154(b) by 283 days.

(21) Appl. No.: 12/336,463

(22) Filed: Dec. 16, 2008

(65) Prior Publication Data

US 2010/0029691 A1   Feb. 4, 2010

Related U.S. Application Data

(60) Provisional application No. 61/086,124, filed on Aug. 4, 2008.

(51) Int. Cl.
*A61K 31/519* (2006.01)
(52) U.S. Cl. .................................. 514/259.41
(58) Field of Classification Search .............. 514/259.41
See application file for complete search history.

(56) References Cited

U.S. PATENT DOCUMENTS

2005/0053654 A1   3/2005   Faham et al.
2006/0127489 A1   6/2006   Crothers et al.

FOREIGN PATENT DOCUMENTS

WO   WO 2006/092812   *   9/2006

OTHER PUBLICATIONS

International Search Report and Written Opinion for PCT/US09/52492, mailed Sep. 28, 2009, 6 pages.

* cited by examiner

*Primary Examiner* — Benjamin Packard
*Assistant Examiner* — Adam C Milligan
(74) *Attorney, Agent, or Firm* — Morrison & Foerster LLP

(57) ABSTRACT

The present invention provides orodispersable tablets and methods of using the same. The tablets and methods are useful, for example, for reducing first pass metabolism of orally administered active agents, enhancing bioavailability of active agents, and/or reducing the time it takes for an active agent to achieve maximal effect in a subject. The tablets, when taken orally, disintegrate or dissolve rapidly such that active agent included in the tablets is absorbed in the buccal cavity. The invention further provides methods of manufacturing any of the tablets disclosed herein and containers that include any of the tablets disclosed herein.

20 Claims, 5 Drawing Sheets

Fig. 1

Schematic Demonstration of a Set-up for LCST Measurement

Fig. 2

750 nm Transmission -vs- Temperature for Various Binders
(2 wt% of polymer in de-ionized water)

Fig. 3
Depression of the LCST of Hydroxypropylcellulose by Various LCST Modifiers

Fig. 4

**Depression of LCST of *Klucel EF* by Various LCST-lowering Electrolytes at 0.02M Concentration**

Fig. 5

Disintegration of Tablets Lacking a Binder

Error bars represent standard deviation of n=3.

FAST ONSET ORODISPERSABLE TABLETS

The present application claims priority to U.S. Provisional Application No. 61/086,124, filed Aug. 4, 2008, which is incorporated by reference herein in its entirety.

FIELD OF THE INVENTION

This invention relates generally to pharmaceutical formulations designed for oral administration and methods of manufacturing the same. More particularly, the invention relates to pharmaceutical formulations designed to disintegrate rapidly in the buccal cavity of a subject and methods of using such formulations to provide fast onset for pharmaceutical agents.

BACKGROUND OF THE INVENTION

The need to take conventional pharmaceutical tablets with the aid of a fluid can be inconvenient or impractical. For example, it can be quite difficult to administer a convention pharmaceutical tablet to a pediatric, geriatric or schizophrenic patient. Fast disintegrating or dissolving tablets (FDDTs) have received a lot of interest because, unlike conventional tablets, they disintegrate and dissolve rapidly in saliva, thereby eliminating the need to be swallowed with the aid of a fluid. Because of this interest, a variety of technologies have been developed for FDDTs. Some tablets can dissolve in saliva remarkably fast, while others comprise formulations that enhance the rate of tablet disintegration in the oral cavity.

Critical attributes for FDDTs are the tablet friability and taste masking, as well as the disintegration or dissolution rate. Usually, the ability to quickly disintegrate or dissolve compromises a tablet's hardness, thereby increasing the difficulty associated with handling. Taste masking is characteristic of FDDTs. Current methods of taste masking with FDDTs include use of sweeteners and flavors, adsorption onto or complexation with carriers, and coacervation and spray coating of drug particles.

Some FDDT technologies also claim an increased bioavailability compared to conventional tablets. Because of rapid tablet disintegration or dissolution in saliva, a large fraction of the pharmaceutical agent contained within the tablet can be absorbed in buccal and pharyngeal regions, thereby minimizing the pre-systemic degradation of the agent. Increased bioavailability may result for pharmaceutical agents that ordinarily experience extensive first pass metabolism.

There remains a need in the art for new rapidly disintegrating tablets that provide fast onset for pharmaceutical agents which, e.g., can be handled without fracturing and manufactured using conventional oral tablet compression.

SUMMARY OF THE INVENTION

The present invention is based, in part, on the discovery that certain combinations of binders, e.g., polymers and modifiers, can be used to produce useful pharmaceutical formulations, such as orodispersable tablets. Accordingly, the present invention provides compositions, including orodispersable tablets having low friability, fast onset, and/or increased bioavailability of the pharmaceutical agents contained therein.

In one aspect, the present invention provides an orodispersable tablet comprising an active agent, a binder, and a modifier. The active agent can be hydrophobic or hydrophilic. For example, the active agent can be substantially insoluble in water. The active agent can be, for example, a small molecule drug, protein, sugar, polysaccharide, nucleic acid, lipid, steroid, hormone, nutritional supplement, growth supplement, electrolyte, or diagnostic agent.

The binder can comprise a polymer, such as a polymer having a relatively low critical solution temperature, e.g., a lower critical solution temperature (LCST). The LCST of the polymer can be, for example, less than about 100° C. The LCST of the polymer can be greater than about 40° C. The polymer can be, for example, a cellulose-based polymer, an acrylamide- or acrylate-based polymer, a polyvinyl polymer, a polyethylene glycol polymer, a polypropylene glycol polymer, a polypeptide polymer, or mixtures thereof.

The modifier can be any suitable entity or composition capable of reducing the critical solution temperature of a polymer, e.g., to about body temperature or lower. For example, the modifier can reduce the critical solution temperature of a polymer to less than 40° C., and preferably less than or about 37° C. The modifier can be an electrolyte, a polyol, a mixture of electrolytes, a mixture of polyols, or any combination thereof.

Electrolyte modifiers can include a cation, such as an inorganic cation. Electrolyte modifiers can also include an anion, such as an organic anion or an inorganic anion. An organic anion can include, for example, one or more carboxylic acid groups, sulfate groups, phosphate groups, hydroxyl groups, or any combination thereof.

A polyol modifier can include an organic molecule comprising two or more hydroxyl groups. A polyol modifier can include, for example, a five- or six-carbon ring structure comprising two or more hydroxyl groups, or a simple sugar, such as a monosaccharide (e.g., a five- or six-carbon monosaccharide) or a disaccharide.

The tablets can further comprise a carrier. For example, the tablets can comprise a carrier for the active agent. The carrier can comprise porous particles, a solubility enhancing agent, a taste-masking agent, or any combination thereof. The carrier can be temperature responsive.

The tablets can further comprise a disintegrant, a lubricant, a taste-masking agent, a bulking agent, or any combination thereof.

The provided tablets can disintegrate rapidly. For example, when administered orally, the tablets can disintegrate in about 60 seconds or less. At the same time, the tablets can have a low friability.

In another aspect, a method for manufacturing a tablet disclosed herein is provided. The method can comprise: granulation of a polymer (e.g., a polymer having a lower critical solution temperature) and a modifier (e.g., a composition capable of reducing the critical solution temperature of the polymer to lower than or about body temperature) to produce a granulated mass; compression of the granulated mass to produce a tablet; and, optionally, color coating the tablet. The granulation can include wet granulation, fluid-bed granulation, roller-compaction granulation, or any combination thereof.

In another aspect, a container comprising a tablet disclosed herein is provided. The container can include, or be accompanied by, an instruction. The instruction can provide, for example, that the tablet is for oral administration, that the tablet disintegrates or dissolves upon contact with saliva, that the active agent is predominantly absorbed in the buccal cavity, that the tablet reduces first pass metabolism of the active agent, that the tablet enhances bioavailability of the active agent, that the tablet reduces the time it takes for the active agent to achieve maximal effect, or any combination thereof.

In another aspect, a method of reducing first pass metabolism of an orally administered active agent in a subject is provided. The method can comprise providing a tablet disclosed herein to the subject, wherein the tablet includes the active agent. The provided tablet, when taken orally, can disintegrate or dissolve rapidly in the buccal cavity of the subject. Upon disintegration or dissolution, absorption of active agent can occur in the buccal cavity of the subject.

In another aspect, a method of enhancing bioavailability of an active agent in a subject is provided. The method can comprise providing a tablet disclosed herein to the subject, wherein the tablet includes the active agent. The provided tablet, when taken orally, can disintegrate or dissolve rapidly in the buccal cavity of the subject. Upon disintegration or dissolution, absorption of active agent can occur in the buccal cavity of the subject.

In another aspect, a method of reducing the time for an active agent to achieve maximal effect in a subject is provided. The method can comprise providing a tablet disclosed herein to the subject, wherein the tablet includes the active agent. The provided tablet, when taken orally, can disintegrate and dissolve rapidly in the buccal cavity of the subject. Upon disintegration and dissolution, absorption of active agent can occur in the buccal cavity of the subject.

In yet another aspect, a method of administering an active agent to a subject is provided. The method can comprise providing a tablet disclosed herein to the subject, wherein the tablet includes the active agent. The tablet can be provided along with instructions to take the tablet orally. The provided tablet, when taken orally, can disintegrate or dissolve rapidly in the buccal cavity of the subject. Upon disintegration or dissolution, absorption of active agent can occur in the buccal cavity of the subject. Absorption of active ingredient in the buccal cavity can reduce first pass metabolism of the active agent, enhance bioavailability of the active agent, and/or reduce the time it takes for the active agent to achieve maximal effect.

BRIEF DESCRIPTION OF THE DRAWINGS

FIG. 2 is a graph showing percent transmission (T %) of 750 nm light through various solutions of LCST polymers as a function of temperature. Each solution is 2 wt % polymer in deionized water. Results for solutions containing hydroxypropylcellulose (Klucel® EF), hydroxypropylmethylcellulose (HPMC E5, HPCM K3), poly(oxyethylene-co-oxypropylene) (Pluronic® F127), methylcellulose (Methocel™ A15), sodium carboxylmethylcellulose (Na CMC 7LF), hydroxyethyl-cellulose (Natrosol® 250L), poly(vinyl acetate-co-vinyl pyrrolidone) (VA 64), and poly(vinyl pyrrolidone K29-32) (Kolidone™ 30) are shown. The cloud point is a measure of the LCST of a polymer and is the temperature at which percent transmission drops to 90% of its value at room temperature (25° C.). The graph shows that the cloud point for hydroxypropylcellulose occurs at about 42° C., while the cloud point for hydroxy-propylmethylcellulose occurs at about 56° C.

DETAILED DESCRIPTION OF THE INVENTION

The present invention provides orodispersable tablets and methods of using the same. The tablets and methods are useful, for example, for reducing first pass metabolism of orally administered active agents, enhancing bioavailability of active agents, and/or reducing the time it takes for an active agent to achieve maximal effect in a subject. The tablets, when taken orally, disintegrate or dissolve rapidly such that active agent included in the tablets is absorbed in the buccal cavity. The invention further provides methods of manufacturing any of the tablets disclosed herein and containers that include any of the tablets disclosed herein.

One of the objectives behind the present invention is to provide a fast disintegrating and fast dissolving tablet composition. Normally, a binder is necessary for a tablet formulation in order to ensure desirable mechanical properties, such as low friability and high hardness. However, the existence of a binder significantly slows down disintegration of the tablet. In an ideal situation, a binder useful for a fast disintegrating composition should not delay tablet disintegration while still providing the needed binding and adhesive properties. Without intending to be bound by any theory, it is believed that a binder comprising a polymer having a lower critical solution temperature (an LCST polymer) loses its binding properties in aqueous medium at a temperature close to or higher than its LCST and undergoes an in situ precipitation or flocculation. Binders commonly used for oral tablets have their LCSTs above 37° C., however, so they do not precipitate or flocculate at body temperature (about 37° C.). The present invention provides, among other things, an LCST modifier in combination with a LCST polymer to reduce the LCST of the LCST polymer below or about 37° C., thereby ensuring fast disintegration. A fast disintegrating or dissolving tablet in accordance with the invention can be directly compressed into a tablet with strong mechanical strength. The tablet is particularly useful for providing a wide range of pharmaceutical agents with a fast onset of pharmaceutical effect.

Accordingly, in one aspect, the invention provides an orodipersable tablet. In certain embodiments, the orodispersable tablet comprises an active agent, a binder, and a modifier.

In certain embodiments, the binder comprises a polymer and the presence of the modifier reduces the critical solution temperature of said polymer.

As used herein, an "orodispersable tablet" is a tablet that, when taken orally, disintegrates in the buccal cavity of a subject. As used herein, the term "disintegrate" means that the tablet breaks down into a number of smaller fragments, none of which have a mass greater than 2% of the mass of the original tablet. In certain embodiments, the orodispersable tablet disintegrates entirely in the buccal cavity of a subject. In other embodiments, a portion of the orodispersable tablet disintegrates in the buccal cavity of a subject. For example, in certain embodiments, at least 25%, 50%, 60%, 70%, 80%, 90%, 95%, or more (by weight) of the orodispersable tablet disintegrates in the buccal cavity of the subject.

In certain embodiments, an orodispersable tablet disintegrates rapidly when administered orally. For example, in certain embodiments, the orodispersable tablets disintegrate in about 90, 80, 70, 60, 50, 45, 40, 35, 30, 25, 20, 15, 10 seconds, or less. In certain embodiments, the disintegration time of the tablet depends upon the size of the tablet. For example, in certain embodiments, the tablet is about 300 to 500 mg in size and disintegrates in about 45 to about 60, about 30 to about 45, about 15 to about 30, or about 5 to about 25 seconds. In other embodiments, the tablet is about 100 to 300 mg in size and disintegrates in about 30 to about 45, about 15 to about 30, about 5 to about 20, or about 1 to about 15 seconds.

As used herein, an "active agent" is an organic or inorganic compound that is physiologically or pharmacologically active. In certain embodiments, an active agent produces a localized or systemic effect in a subject. For example, an active agent can be capable of affecting a physiological system, a cell, or a molecule found in a subject. As used herein, a "subject" is any animal, including a human, primate, domestic household or farm animal, such as a cat, dog, horse, cow, pig, sheep, and goat, a laboratory animal, such as a mouse, rat, guinea pig, rabbit or monkey, a zoo animal, such as a lion, tiger, bear, elephant, giraffe, hippo or rhinoceros, a wild animal, a warm-blooded mammal, a cold-blooded animal, a bird, etc.

In certain embodiments, an active agent has desirable medicinal properties that can be used to treat a condition, such as pain, nausea or menopause, a disorder, such as a mental disorder (e.g., anxiety, paranoia, bipolar, schizophrenia), a disease, such as Alzheimer's disease, or an infection. In certain embodiments, an active agent has desirable physiological properties that can be used to foster or maintain the physiological health of a subject. In certain embodiments, an active agent has desirable mental properties that can be used to foster or maintain the mental health or acuity of a subject. In certain embodiments, an active agent can act upon peripheral nerves, synaptic sites, neuroeffector junctional sites, adrenergic receptors, cholinergic receptors, skeletal muscles, the cardiovascular system, smooth muscles, the blood circulatory system, endocrine and hormone systems, the immunological system, the reproductive system, the skeletal system, autacoid systems, the alimentary and excretory systems, the histamine system, or the central nervous system of a subject.

In certain embodiments, an active agent is a drug, such as a small molecule drug, a protein drug, a nucleic acid drug, a vitamin, a food, a food extract, a food supplement, an antiacid, an antibiotic, an electrolyte, or a diagnostic agent. For example, an active agent can be a protein, enzyme, enzyme inhibitor, hormone, polynucleotide, nucleoprotein, polysaccharide, glycoprotein, lipoprotein, polypeptide, steroid, hypnotic agent, sedative, psychic energizer, tranquilizer, anticonvulsant, antidepressant, muscle relaxant, antiparkinson agent, analgesic, anti-inflammatory, antihystamine, local anesthetic, muscle contractant, antimicrobial, antimalarial, antiviral, antibiotic, antiobesity agent, hormonal agent, including contraceptives, sympathomimetic, diuretic, lipid regulating agent, antiandrogenic agent, antiparasitic, neoplastic, antineoplastic, antihyperglycemic, hypoglycemic, nutritional agent or supplement, growth supplement, fat, ophthalmic, or antienteritis agent.

In certain embodiments, an active agent is hydrophobic. In certain embodiments, an active agent is hydrophobic and substantially insoluble in water. As used herein, "substantially insoluble in water" means that the solubility of the active agent is less than about 1 mg/ml in water. In certain embodiments, an active agent has a solubility of less than about 0.5 mg/ml, less than about 0.1 mg/ml, or even less than 0.1 μg/ml. In other embodiments, an active agent is hydrophilic. For example, the active agent can have a solubility in water greater than or equal to 1 mg/ml.

In certain embodiments, an active agent is selected from the group consisting of fentanyl, sufentanil, zaleplon, zolpidem (e.g., zolpidem tartrate), zopiclone, risperidone, sumatriptan (e.g., sumatriptan succinate), amphentamine, dextroamphentamine, dextromethorphan, donepezil hydrochloride, ergotamine (e.g., ergotamine tartrate), granisetron hydrochloride, ondansetron, ramosetron hydrochloride, prochlorperazine edisylate, ferrous sulfate, albuterol, aminocaproic acid, mecamylamine hydrochloride, procainamide hydrochloride, amphetamine sulfate, methamphetamine hydrochloride, benzphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, theophylline cholinate, cephalexin hydrochloride, diphenidol, meclizine hydrochloride, prochlorperazine maleate, phenoxybenzamine, thiethylperazine maleate, anisindione, diphenadione erythrityl tetranitrate, digoxin, isoflurophate, acetazolamide, nifedipine, methazolamide, bendroflumethiazide, chlorpropamide, glipizide, glyburide, gliclazide, tobutamide, chlorproamide, tolazamide, acetohexamide, metformin, troglitazone, orlistat, bupropion, nefazodone, tolazamide, chlormadinone acetate, phenaglycodol, allopurinol, aluminum aspirin, methotrexate, acetyl sulfisoxazole, hydrocortisone, hydrocorticosterone acetate, cortisone acetate, dexamethasone and its derivatives such as betamethasone, triamcinolone, methyltestosterone, 17-β-estradiol, ethinyl estradiol, ethinyl estradiol 3-methyl ether, prednisolone, 17-β-hydroxyprogesterone acetate, 19-norprogesterone, norgestrel, norethindrone, norethisterone, norethiederone, progesterone, norgesterone, norethynodrel, terfandine, fexofenadine, aspirin, acetaminophen, indomethacin, naproxen, fenoprofen, sulindac, indoprofen, nitroglycerin, isosorbide dinitrate, propranolol, timolol, atenolol, alprenolol, cimetidine, clonidine, imipramine, levodopa, selegiline, chlorpromazine, methyldopa, dihydroxyphenylalanine, calcium gluconate, ketoprofen, ibuprofen, cephalexin, erythromycin, haloperidol, zomepirac, ferrous lactate, vincamine, phenoxybenzamine, diltiazem, milrinone, captropril, mandol, quanbenz, hydrochlorothiazide, ranitidine, flurbiprofen, fenbufen, fluprofen, tolmetin, alclofenac, mefenamic, flufenamic, difuninal, nimodipine, nitrendipine, nisoldipine, nicardipine, felodipine, lidoflazine, tiapamil, gallopamil, amlodipine, mioflazine, lisinopril, enalapril, captopril, ramipril, enalaprilat, famotidine, nizatidine, sucralfate, etintidine, tetratolol, minoxidil, chlordiazepoxide, diazepam, amitriptyline, and imipramine, and pharmaceutical salts of these active agents.

In certain embodiments, an active agent is selected from the group consisting of fentanyl (e.g., free base or fentanyl citrate), sufentanil (e.g., free base or sufentanil citrate), zaleplon, zolpidem (e.g., zolpidem tartrate), zopiclone, risperidone, sumatriptan (e.g., sumatriptan succinate), amphentamine, dextroamphentamine, dextromethorphan, donepezil (e.g., donepezil hydrochloride), ergotamine (e.g., ergotamine tartrate), granisetron (e.g., granisetron hydrochloride), methylphenidate (e.g., methylphenidate hydrochloride), ondansetron, and ramosetron (e.g., ramosetron hydrochloride).

In certain embodiments, the active agent comprises fentanyl (e.g., free base or fentanyl citrate). In certain embodiments, the amount of fentanyl (free base equivalent) in a tablet is about 0.05 mg to about 2.0 mg, about 0.1 mg to about 1.6 mg, or about 0.2 mg to about 0.8 mg. In other embodiments, the amount of fentanyl (free base equivalent) in a tablet is about 0.1 mg, 0.2 mg, 0.3 mg, 0.4 mg, 0.6 mg, 0.8 mg, 1.2 mg, or 1.6 mg.

In certain embodiments, the active agent comprises sufentanil (e.g., free base of sufentanil citrate). In certain embodiments, the amount of sufentanil (free base equivalent) is about 0.01 mg to about 0.8 mg, or about 0.02 mg to about 0.4 mg. In other embodiments, the about of sufentanil (free base equivalent) in a tablet is about 0.05 mg.

In certain embodiments, the active agent comprises zaleplon. In certain embodiments, the amount of zaleplon in a tablet is about 1.0 mg to about 40 mg, or about 4.0 mg to about 20 mg. In other embodiments, the amount of zaleplon in a tablet is about 5 mg or about 10 mg.

In certain embodiments, the active agent comprises zolpidem (e.g., zolpidem tartrate). In certain embodiments, the amount of zolpidem tartrate in a tablet is about 1.0 mg to about 40 mg, or about 4.0 mg to about 12.5 mg. In other embodiments, the amount of zolpidem tartrate in a tablet is about 5 mg or about 10 mg.

In certain embodiments, the active agent comprises risperidone. In certain embodiments, the amount of risperidone in a tablet is about 0.1 mg to about 8.0 mg, or about 0.2 mg to about 5.0 mg. In other embodiments, the amount of risperidone in a tablet is about 0.25 mg, about 0.5 mg, about 1.0 mg, about 2.0 mg, about 3.0 mg, or about 4.0 mg.

In certain embodiments, the active agent comprises sumatriptan (e.g., free base or sumatriptan succinate). In certain embodiments, the amount of sumatriptan (free base equivalent) in a tablet is about 10 mg to about 200 mg, or about 20 mg to about 120 mg. In other embodiments, the amount of sumatriptan (free base equivalent) in a tablet is about 25 mg, about 50 mg, about 85 mg, or about 100 mg.

In certain embodiments, the active agent comprises amphentamine. In certain embodiments, the amount of amphentamine in a tablet is about 5 mg to about 50 mg, or about 10 mg to about 40 mg. In other embodiments, the amount of amphentamine in a tablet is about 20 mg or about 30 mg.

In certain embodiments, the active agent comprises dextroamphentamine. In certain embodiments, the amount of dextroamphentamine in a tablet is about 1 mg to about 30 mg, or about 2 mg to about 20 mg. In other embodiments, the amount of dextroamphentamine in a tablet is about 2.5 mg, about 5.0 mg, about 10 mg, or about 35 mg.

In certain embodiments, the active agent comprises dextromethorphan. In certain embodiments, the amount of dextromethorphan in a tablet is about 5 mg to about 90 mg, or about 10 mg to about 60 mg. In other embodiments, the amount of dextromethorphan in a tablet is about 10 mg or about 15 mg.

In certain embodiments, the active agent comprises donepezil (e.g., donepezil hydrochloride). In certain embodiments, the amount of donepezil in a tablet is about 1 mg to about 20 mg, or about 2 mg to about 15 mg. In other embodiments, the amount of donepezil in a tablet is about 5 mg or about 10 mg.

In certain embodiments, the active agent comprises ergotamine (e.g., ergotamine tartrate). In certain embodiments, the amount of ergotamine in a tablet is about 0.1 mg to about 10 mg, or about 0.5 mg to about 5 mg. In other embodiments, the amount of ergotamine in a tablet is about 2 mg.

In certain embodiments, the active agent comprises granisetron (e.g., granisetron hydrochloride). In certain embodiments, the amount of granisetron in a tablet is about 0.1 mg to about 10 mg, or about 0.5 mg to about 5 mg. In other embodiments, the amount of granisetron in a tablet is about 1 mg or about 2 mg.

In certain embodiments, the active agent comprises methylphenidate (e.g., methylphenidate hydrochloride). In certain embodiments, the amount of methylphenidate hydrochloride in a tablet is about 1.0 mg to about 90 mg, or about 2.0 mg to about 75 mg. In other embodiments, the amount of methylphenidate hydrochloride in a tablet is about 5 mg, about 10 mg, about 20 mg, about 30 mg, about 40 mg, about 50 mg, or about 60 mg.

In certain embodiments, the active agent comprises ondansetron (e.g., odansetron hydrochloride). In certain embodiments, the amount of ondansetron in a tablet is about 1.0 mg to about 20 mg, or about 2.0 mg to about 10 mg. In other embodiments, the amount of ondansetron in a tablet is about 4 mg or about 8 mg.

In certain embodiments, the active agent comprises ramosetron (e.g., ramosetron hydrochloride). In certain embodiments, the amount of ramosetron in a tablet is about 0.05 mg to about 2 mg, or about 0.1 mg to about 1 mg. In other embodiments, the amount of ramosetron in a tablet is about 0.15 mg, about 0.3 mg, or about 0.6 mg.

In certain embodiments, the active agent comprises a combination of different active agents. For example, in certain embodiments, the active agent is a combination of two or more active agents disclosed herein (e.g., a combination of amphentamine and dextroamphentamine). In certain embodiments, the active agent is a combination of two or more complimentary active agents (e.g., combinations of drugs that are often prescribed or taken together). For example, in certain embodiments, the active agent comprises fentanyl in combination with another analgesic (e.g., morphine, codine, etc.). In other embodiments, the active agent comprises sufentanil in combination with another analgesic (e.g., morphine, codine, etc.). In other embodiments, the active agent comprises risperidone in combination with a SSRI (e.g., sertraline, fluvoxamine, etc.), an anticonvulsant (e.g., clobazam), a mood stabilizer (e.g., lithium, valproic acid, valproate, etc.), an anti-psychotic (e.g., clozapine), or an anti-anxiety agent (e.g., lorazepam). In other embodiments, the active agent comprises sumatriptan (e.g., sumatriptan succinate) in combination with a non-steroidal anti-inflammatory drug (e.g., naproxen). In other embodiments, the active agent comprises dextromethorphan in combination with quinidine, morphine, promethazine, or phenylpropanolamine and/or brompheniramine. In other embodiments, the active agent comprises donepezil (e.g., donepezil hydrochloride) in combination with an anti-Alzheimer's agent (e.g., memantine). In other embodiments, the active agent comprises ergotamine (e.g., ergotamine tartrate) in combination with caffeine or an agent used to treat menopause symptoms (e.g., belladonna and/or phenobarbital). In other embodiments, the active agent comprises granisetron (e.g., granisetron hydrochloride) in combination with an anti-nausea agent (e.g., dexamethasone). In other embodiments, the active agent comprises ondansetron in combination with an anti-nausea agent (e.g., dexamethasone). In still other embodiments, the active agent comprises ramosetron (e.g., ramosetron hydrochloride) in combination with an anti-nausea agent (e.g., dexamethasone).

As used herein, a "binder" is a substance that functions to bind and hold together the various constituents of a tablet. In certain embodiments, a binder of the invention provides a tablet that has low friability and/or high hardness. As used herein, a tablet that has low friability exhibits no more than 2% weight loss, on average, when tested on a friability tester, as described in Example 9, infra. In certain embodiments, a binder of the invention is capable of providing a tablet that has 1.5%, 1.0%, 0.5%, 0.1%, or less weight loss, on average. As used herein, a tablet that has high hardness has a hardness of at least 0.5, as measured on a tablet hardness tester, as described in Example 9. In certain embodiments, the hardness of the tablet is at least 1.0, 1.5, 2.0, 2.5, 2.75, 3.0, 3.25, 3.5, 3.75, 4.0, 4.25, 4.5, or higher.

In certain embodiments, the tablet has a disintegration time of 60, 50, 45, 40, 35, 30, 25, 20 seconds or less when tested on a disintegration tester, as described in Example 3, infra; a friability of 98%, 98.5%, 99%, 99.5%, 99.8%, 99.9%, or higher when tested on a friability tester, as described in Example 9; and a hardness of 1.5, 2.0, 2.5, 3.0, 3.25, 3.5, 3.75, 4.0, 4.25, 4.5 or higher when tested on a hardness tester, as described in Example 9.

In certain embodiments, the binder comprises a polymer having a critical solution temperature (e.g., a lower critical solution temperature). In other embodiments, the binder consists essentially of a polymer having a critical solution temperature (e.g., a lower critical solution temperature). As used herein, the "critical solution temperature" of a polymer is the temperature at and above which the polymer starts to precipitate or flocculate in distilled water. In general, a polymer having a critical solution temperature exhibits decreasing solubility in deionized water as temperature approaches its critical solution temperature and loses its binding properties when temperature reaches its critical solution temperature. Depending upon the particular polymer, the critical solution temperature can be relatively high or low, as compared to body temperature (e.g., human body temperature). As used herein, a "polymer having a lower critical solution temperature" or an "LCST polymer" is a polymer that exhibits decreasing solubility in solution as the temperature of the solution increases. In certain embodiments, the critical solution temperature of an LCST polymer is less than or equal to 100° C., 90° C., 80° C., 70° C., 65° C., 60° C., 55° C., 50° C., or 45° C. In certain embodiments, the critical solution temperature of an LCST polymer is greater than or equal to 37° C., 40° C., or 45° C. Thus, in certain embodiments, LCST polymers have a critical solution temperature that lies within the range of 37° C. to 100° C., or any narrower range within the range of 37° C. to 100° C.

In certain embodiments, the LCST polymer is a cellulose-based polymer. As used herein, a "cellulose-based polymer" is a polymer that comprises cellulose or a derivative of cellulose. Cellulose-based polymers include, but are not limited to, alkylcellulose (e.g., methylcellulose), hydroxyalkylcellulose (e.g., hydroxypropylcellulose or hydroxyethylcellulose), and hydroxyalkylalkylcellulose (e.g., hydroxypropylmethylcellulose).

In certain embodiments, the cellulose-based polymer is a low molecular weight polymer. For example, in certain embodiments, the cellulose-based polymer is methylcellulose, wherein the methylcellulose has a molecular weight of about 8,000 to about 18000 Daltons, or about 10,000 to about 14,300 Daltons. In other embodiments, the cellulose-based polymer is hydroxypropylcellulose, wherein the hydroxypropylcellulose has a molecular weight of about 70,000 to about 90,000 Daltons, or about 75,000 to about 85,000 Daltons, or about 80,000 Daltons. In still other embodiments, the cellulose-based polymer is hydroxypropylmethyl-cellulose, wherein the hydroxypropylmethylcellulose has a molecular weight of about 7,000 to about 13,000 Daltons, or about 9,600 to about 11,300 Daltons.

In certain embodiments, the cellulose-based polymer is hydroxypropylcellulose having a degree of substitution less than 80.5% inclusive. Preferred types of hydroxypropylcellulose include Klucel® EF and Klucel® EXF. In other embodiments, the cellulose-based polymer is hydroxypropylmethylcellulose having a degree of methoxyl substitution of about 1.0 to about 2.2 (e.g., about 1.12 to about 1.64, or about 1.78 to about 2.03) and a degree of hydroxypropyl substitution of about 0.05 to 0.4 (e.g., about 0.10 to about 0.33, or about 0.18 to about 0.34). Preferred types of hydroxypropylmethylcellulose include HPMC K3 and HPCM E5.

In certain embodiments, the LCST polymer is a polyvinyl polymer. As used herein, a "polyvinyl polymer" is a polymer that comprises polymerized vinyl groups. Polyvinyl polymers include, but are not limited to, poly(vinyl alcohol-co-vinyl acetate), poly(vinyl acetate-co-vinyl pyrrolidone), poly (vinyl pyrrolidone), and poly(vinylmethyl ether).

In certain embodiments, the LCST polymer is an acrylamide/acrylate-based polymer. As used herein, an acrylamide/acrylate-based polymer is a polymer that comprises polymerized acrylamide and/or acrylate groups. Acrylamide/acrylate-based polymers include, but are not limited to, polymethacrylic acid long alkyl chain quaternary salt, poly (alkyl acrylate), poly(alkylacrylamide), and poly(N-isopropyl-acrylamide).

In certain embodiments, the LCST polymer is a polyethylene glycol-containing polymer. As used herein, a polyethylene glycol-containing polymer is a polymer that comprises polyethylene glycol. Polyethylene glycol-containing polymers include, but are not limited to, poly(ethylene glycol) monoether and poly(ethylene glycol-co-propylene glycol).

In certain embodiments, the LCST polymer is a polypropylene glycol-containing polymer. As used herein, a polypropylene glycol-containing polymer is a polymer that comprises polypropylene glycol. Polypropylene glycol-containing polymers include, but are not limited to, poly (propylene glycol) and poly(ethylene glycol-co-propylene glycol).

In certain embodiments, the LCST polymer is a polypeptide polymer. As used herein, a polypeptide polymer is a polymer that comprises multiple peptide bonds. Polypeptide polymers include, but are not limited to, proteins (e.g., proteins containing naturally occurring and non-naturally occurring amino acids) and poly(L-proline).

In certain embodiments, the polymer is an LCST polymer selected from the group consisting of alkylcellulose, hydroxyalkylcellulose, hydroxyalkylalkylcellulose, poly(vinyl alcohol co-vinyl acetate), poly(vinyl acetate co-vinyl pyrrolidone), poly(vinyl pyrrolidone), poly(vinyl methyl ether), poly(alkyl alkylacrylate), polymethacrylic acid long alkyl chain quaternary salt, poly(alkylacrylamide), poly(N-isopropyl-acrylamide), polyethylene glycol (PEG), polypropylene glycol (PPG), poly(ethylene glycol co-propylene glycol), and polypeptides In other embodiments, the polymer is an LCST polymer selected from the group consisting of alkylcellulose, hydroxyalkylcellulose, hydroxyalkylalkylcellulose, poly(vinyl acetate co-vinyl pyrrolidone), and poly(ethylene glycol co-propylene glycol).

In other embodiments, the polymer is an LCST polymer selected from the group consisting of methyl cellulose, hydroxypropylcellulose, hydroxypropylmethylcellulose, and poly(vinyl acetate co-vinyl pyrrolidone).

In still other embodiments, the polymer is an LCST polymer selected from the group consisting of hydroxypropylcellulose and hydroxypropylmethylcellulose.

In certain embodiments, the binder comprises a single polymer, wherein the polymer is an LCST polymer. In certain embodiments, the binder consists essentially of a single LCST polymer. In other embodiments, the binder comprises two or more polymers, wherein the polymers are LCST polymers. In other embodiments, the binder consists essentially of two or more LCST polymers.

In certain embodiments, the binder comprises an LCST polymer and another binding substance, wherein the other binding substance is not an LCST polymer. In certain embodiments, the other binding substance is a non-LCST polymer. In certain embodiments, the amount of other binding substance is less than about 10%, 5%, 4%, 3%, 2%, 1%, or less of the total amount of binder in the tablet.

In certain embodiments, the binder makes up 1% to 25%, 2% to 20%, 3% to 15%, 4% to 10%, or about 5% of the weight of the tablet. In certain embodiments, the binder comprises an LCST polymer, wherein the LCST polymer makes up 1% to 25%, 2% to 20%, 3% to 15%, 4% to 10%, or about 5% of the weight of the tablet.

As used herein, a "modifier" is an organic or inorganic compound that, when mixed with an LCST polymer, is capable of reducing the critical solution temperature of the polymer to 40° C. or lower. In preferred embodiments, the modifier is capable of reducing the critical solution temperature of the LCST polymer to 39° C., 38° C., 37° C., 36° C., 35° C., or lower.

In certain embodiments, the modifier is an electrolyte. As used herein, an "electrolyte" is a salt that comprises a cation and an anion. In certain embodiments, the electrolyte comprises an inorganic cation (e.g., a divalent or monovalent inorganic cation). In certain embodiments, the cation is selected from the group consisting of calcium, magnesium, potassium, and sodium.

In certain embodiments, the modifier is an electrolyte, wherein the electrolyte comprises an organic or inorganic anion. In certain embodiments, the anion is organic and comprises at least one carboxylate group, at least one hydroxyl group, or a combination thereof. In certain embodiments, the anion is organic and is selected from the group consisting of acetate, citrate, lactate, aspartate, sorbate, ascorbate, and propionate. In other embodiments, the anion is inorganic and is selected from the group consisting of phosphate, sulfate, chloride, hydroxide, carbonate, bicarbonate, bisulfite, and metabisulfite.

In certain embodiments, the modifier is selected from the group consisting of calcium acetate, calcium citrate, calcium lactate, calcium phosphate, calcium sulfate, calcium sulfate dihydrate, magnesium acetate, magnesium aspartate, magnesium cloride, magnesium hydroxide, magnesium phosphate, magnesium sulfate, potassium chloride, potassium citrate, potassium phosphate monobasic, potassium phosphate dibasic, potassium sorbate, sodium acetate, sodium ascorbate, sodium bicarbonate, sodium bisulfite, sodium chloride, sodium citrate, sodium hydroxide, sodium lactate, sodium metabisulfite, sodium phosphate monobasic, sodium phosphate dibasic, sodium propionate, and sodium sulfate.

In other embodiments, the modifier is selected from the group consisting of calcium citrate, calcium sulfate (e.g., anhydrous or dihydrate), magnesium chloride, magnesium sulfate, sodium chloride, sodium citrate, sodium sulfate, and potassium phosphate (e.g., monobasic or dibasic).

In other embodiments, the modifier is selected from the group consisting of calcium sulfate (e.g., anhydrous or dihydrate), magnesium sulfate, potassium phosphate (e.g., monobasic or dibasic) and sodium citrate.

In still other embodiments, the modifier is selected from the group consisting of calcium sulfate (e.g., anhydrous or dihydrate) and potassium phosphate (e.g., monobasic or dibasic).

In certain embodiments, the modifier is a polyol. As used herein, a "polyol" is an organic molecule comprising two or more hydoxyl groups. In certain embodiments, a polyol modifier comprises a five- or six-carbon ring structure and two or more hydroxyl groups. In certain embodiments, a polyol modifier consists essentially of a five- or six-carbon ring structure and two or more hydroxyl groups. In other embodiments, a polyol modifier comprises a simple sugar, such as a monosaccharide (e.g., a five- or six-carbon monosaccharide) or a disaccharide. Polyol modifiers include, but are not limited to, aldohexoses, aldopentoses, fructose, galactose, lactose, maltose, sucrose, maltodextrin, lactisol, maltitol, mannitol, sorbitol, and xylitol.

In certain embodiments, the modifier is selected from the group consisting of glucose, fructose, galactose, lactose, maltose, sucrose, maltodextrin, mannitol, sorbitol, and xylitol.

In other embodiments, the modifier is selected from the group consisting of glucose, lactose, mannitol, sorbitol, and xylitol.

In still other embodiments, the modifier is selected from the group consisting of mannitol and xylitol.

In certain embodiments, the modifier comprises two or more electrolytes (e.g., electrolyte modifiers disclosed herein). In other embodiments, the modifier comprises two or more polyols (e.g., polyol modifiers disclosed herein). In still other embodiments, the modifier comprises at least one electrolyte and at least one polyol.

In certain embodiments, for example, the modifier comprises an electrolyte selected from the group consisting of calcium sulfate (e.g., anhydrous or dihydrate), magnesium sulfate, potassium phosphate (e.g., monobasic or dibasic) and sodium citrate and a polyol selected from the group consisting of glucose, lactose, mannitol, sorbitol, and xylitol. In other embodiments, the modifier comprises an electrolyte selected from the group consisting of calcium sulfate (e.g., anhydrous or dihydrate) and potassium phosphate (e.g., monobasic or dibasic) and a polyol selected from the group consisting of mannitol and xylitol. In still other embodiments, the modifier comprises calcium sulfate anhydrous and mannitol. In still other embodiments, the modifier comprises potassium phosphate monobasic and mannitol. In certain embodiments, the modifier comprises an electrolyte and a polyol, wherein the ratio of electrolyte to polyol is about 2:1 to about 1:2, about 1.5:1 to about 1:1.5, about 1.4:1 to about 1:1.2, about 1.3:1 to about 1:1.1, or about 1.2:1 to about 1:1.

In certain embodiments, the modifier makes up about 40% to about 90%, about 50% to about 88%, about 60% to about 86%, or about 65% to about 85% of the weight of the tablet.

In certain embodiments, the ratio of modifier to binder is about 40:1 to about 1:2, or about 30:1 to about 2:1, or about 20:1 to about 5:1, about 20:1 to about 10:1, or about 18:1 to about 12:1. In other embodiments, the ratio of binder to modifier is about 5:1 to 2:1.

In certain embodiments, the ratio of modifier to polymer (e.g., LCST polymer) is about 40:1 to about 1:2, or about 30:1 to about 2:1, or about 20:1 to about 5:1, about 20:1 to about 10:1, or about 18:1 to about 12:1. In other embodiments, the ratio of polymer (e.g., LCST polymer) to modifier is about 5:1 to 2:1.

In certain embodiments, the orodispersable tablets further comprise a carrier for the active agent. In certain embodiments, the carrier comprises porous particles, a solubility enhancing agent, a flavor-masking agent, or any combination thereof.

Porous particles suitable for use as carriers include, but are not limited to particles made from calcium hydrogen phosphate (e.g., Fujicalin® SG or Fujicalin® S), magnesium aluminometasilicate (e.g., Neusilin™ US2), fused silicon dioxide (e.g., Aerosil® or Cab-O-Sil®), or any combination of such particles. In certain embodiments, the porous particles constitute about 10% to about 90%, about 20% to about 80%, about 30% to about 70%, or about 40% to about 60% of the weight of the tablet. In other embodiments, the porous particles constitute about 1% to about 20%, about 5% to about 15%, about 8% to about 12%, or about 10% of the weight of the tablet.

Solubility enhancing agents suitable for use as carriers include, but are not limited to, acetylated monoglycerides, polyoxyethylenated vitamin E (e.g., vitamin E TPGS), surfactants comprising polyoxyethylene, polymers (e.g., polyvinylpyrrolidone) and mixtures thereof. Suitable polyoxyethylenated surfactants include polyoxyethylenated oils, polyoxyethylenated fatty acids, polyoxyethylenated sorbitan fatty acids, polyoxyethylenated alcohols, and polyoxyethylenated ethers. Examples of polyoxyethylenated oils include, but are not limited to, polyoxyethylenated castor oil comprising at least 9, 15, 20, 25, 35, 40, 45, 52, or more moles of ethylene oxide per mole of castor oil (e.g., Cremophor EL®). Examples of polyoxyethylenated sorbitan fatty acids include, but are not limited to, polyoxyethylenated sorbitan palmitate (e.g., polyoxyethylenated sorbitan monopalmitate comprising 5, 10, 15, 20, or more moles of ethylene oxide per mole of sorbitan monopalmitate), polyoxyethylenated sorbitan oleate (e.g., polyoxyethylenated sorbitan monooleate comprising 5, 10, 15, 20, or more moles of ethylene oxide per mole of sorbitan monooleate (e.g., Tween 80®)), and polyoxyethylenated sorbitan stearate (e.g., polyoxyethylenated sorbitan monostearate comprising 4, 10, 15, 20, or more moles of ethylene oxide per mole of sorbitan monostearate or polyoxyethylenated sorbitan tristearate comprising 4, 10, 15, 20, or more moles of ethylene oxide per mole of sorbitan tristearate). Examples of polyoxyethylenated fatty acids include, but are not limited to, polyoxyethylenated stearic acid (e.g., polyoxyethylenated stearic acid comprising 8, 15, 20, 30, 40, or more moles of ethylene oxide per mole of stearic acid), and polyoxyethylenated 12-hydroxystearate (e.g., polyoxyethylenated 12-hydroxystearate comprising 10, 15, 20, or more moles of ethylene oxide per mole of 12-hydroxystearate (e.g., Solutol® HS-15)). Examples of polyoxyethylenated alcohols include, but are not limited to, polyoxyethylenated stearyl alcohol (e.g., polyoxyethylenated stearyl alcohol comprising 2, 4, or more moles of ethylene oxide per mole of stearyl alcohol), and polyoxyethylenated oleyl alcohol (e.g., polyoxyethylenated oleyl alcohol comprising 2, 4, or more moles of ethylene oxide per mole of oleyl alcohol). Examples of polyoxyethylenated ethers include, but are not limited to, polyoxyethylenated lauryl ether.

In certain embodiments, the solubility enhancing agents form micelles. In other embodiments, the solubility enhancing agents are self-emulsifying. For example, in certain embodiments, the self-emulsifying solubility enhancing agents are a mixture of surfactants (e.g., polyoxyethylenated surfactants, as described above) and acetylated monoglycerides. In certain embodiments, the self-emulsifying solubility enhancing agents are a mixture of polyoxyethylenated castor oil (e.g., Cremophor EL®) and acetylated monoglycerides (e.g., Myvacet™ 9-45). In certain embodiments, the ratio of surfactant to acetylated monoglyceride in a self-emulsifying surfactant is about 3:1 to about 1:1, about 2:1 to about 1:1, about 1.5:1 to about 1:1, or about 1:1. In other embodiments, the ratio of surfactant to acetylated monoglyceride in a self-emulsifying surfactant is about 1:1 to about 1:3, about 1:1 to about 1:2, or about 1:1.5 to about 1:1.

In certain embodiments, the solubility enhancing agents constitute about 1% to about 25%, about 2% to about 20%, about 3% to about 15%, about 4% to about 12%, about 5% to about 10%, or about 6% to about 8% of the weight of the tablet.

In certain embodiments, the tablet comprises both porous particles and solubility enhancing agents. For example, in certain embodiments, the tablet comprises calcium hydrogen phosphate particles (e.g., Fujicalin® SG or Fujicalin® S) in combination with polyoxyethylenated surfactant (e.g., a polyoxyethylenated fatty acid, such as polyoxyethylenated 12-hydroxystearate (e.g., Solutol® HS-15)). In certain embodiments, the tablet comprises about 5% to about 15% porous particles in combination with about 5% to 10% polyoxyethylenated surfactant.

In certain embodiments, the carrier is temperature responsive. As used herein, a "temperature responsive" carrier is a substance that forms a solid or gel at room temperature (e.g., about 22° C. to about 28° C.) but melts at body temperature (e.g., in the buccal cavity of a subject). Temperature responsive carriers include, but are not limited to, polyoxyethylenated 12-hydroxystearate (e.g., Solutol® HS-15) and mixtures of polyoxyethylenated castor oil (e.g., Cremophor EL®) or polyoxyethylenated sorbitan monooleate (e.g., Tween 80®) with polyoxyethylenated vitamin E (e.g., vitamin E TPGS).

In certain embodiments, the temperature sensitive carrier constitutes about 1% to about 25%, about 2% to about 20%, about 3% to about 15%, about 4% to about 12%, about 5% to about 10%, or about 6% to about 8% of the weight of the tablet.

In certain embodiments, the tablets further comprise a disintegrant, a lubricant, a taste-masking agent, a bulking agent, a texture agent, or any combination thereof. Suitable disintegrants include, but are not limited to, natural starches (e.g., maize or potato starch), modified starches (e.g., carboxymethylstarch or sodium starch glycolate), starch derivatives (e.g., amylose), cross-linked polyvinyl pyrrolidones, cross-linked celluloses (e.g., cross-linked sodium carboxylmethylcellulose (i.e., Croscarmellose sodium)), alginic acid, sodium alginate, microcrystalline cellulose, and methacrylic acid-divinylbenzene copolymer salts. In certain embodiments, the amount of disintegrant present in a tablet is about 1% to about 20%, about 2% to about 10%, about 3% to about 8%, about 4% to about 6%, or about 5% of the weight of the tablet.

Suitable lubricants include, but are not limited to, magnesium stearate and stearic acid. In certain embodiments, the amount of lubricant present in a tablet is about 0.1% to about 2.0%, or about 0.2% to about 1.5%, or about 0.5% to about 1.0% of the weight of the tablet.

Suitable taste-masking agents include, but are not limited to, aspartame, sodium saccharinate, other flavoring agents, including peppermint oil, spearmint oil and lemon, orange, or cherry powder, and polymers. In certain embodiments, the taste-masking polymer comprises a hydroxyalkylcellulose polymer (e.g., hydroxypropylcellulose or hydroxymethylcellulose) or a polyvinylpyrrolidone polymer (e.g., PVP k12). In other embodiments, the taste-masking polymer comprises a methacrylate polymer (e.g., dimethyl-aminoethyl methacrylate, such as Eudragit® E100) or an acrylate polymer (e.g., meth-/acrylates, such as Eudragit® NE). In certain embodiments, the taste-masking polymer comprises a methacrylate polymer in combination with an acrylate polymer, wherein the ratio of methacrylate polymer to acrylate polymer is about 15:1 to about 2:1, about 12:1 to about 4:1, about 10:1 to about 6:1, or about 9:1.

In certain embodiments, the taste-masking agent is spray-dried with the active agent so as to encapsulate the active agent. In other embodiments, the taste-masking agent is mixed with the active agent and absorbed to porous particles.

In certain embodiments, the amount of taste-masking agent present in a tablet is about 0.1% to about 20%, about 1% to about 15%, about 2% to about 12%, about 3% to about 10%, or about 5% to about 8% of the weight of the tablet. In certain embodiments, the tablet comprises about 5% to about 15% porous particles in combination with about 5% to 10% taste-masking agent.

Suitable bulking agents include, but are not limited to, microcrystalline cellulose. In certain embodiments, no bulking agent is needed because the LCST modifiers disclosed herein provide sufficient bulking material. In certain embodiments, the amount of bulking agent present in a tablet is about 0.5% to about 20%, or about 1% to about 18%, or about 2% to about 15%, or about 5% to about 10%.

Suitable texture agents include, but are not limited to, glycine. In certain embodiments, the amount of texture agent present in a tablet is about 0.1% to about 6%, about 1% to about 5%, about 2% to about 4%, or about 3%.

In certain embodiments, the tablet comprises an active agent, a binder, a modifier, a disintegrant, a taste-masking agent, a texture agent, and a lubricant, wherein the amount of active agent present in the tablet is about 0.5% to about 2.5%, the amount of binder present in the tablet is about 2% to about 8%, the amount of modifier present in the tablet is about 70% to about 88%, the amount of disintegrant present in the tablet is about 2% to about 8%, the amount of taste-masking agent present in the tablet is about 0.5% to about 2%, the amount of texture agent present in the tablet is about 0.5% to about 5%, and the amount of lubricant in the tablet is about 0.1% to about 1%, wherein the percentages are based upon the final weight of the tablet. In certain related embodiments, the active agent comprises risperidone, the binder comprises hydroxypropylcellulose, and the modifier comprises calcium sulfate anhydrous or potassium phosphate monobasic in combination with mannitol. In other related embodiments, the disintegrant comprises cross-linked sodium carboxylmethylcellulose and the lubricant comprises magnesium stearate. In still other related embodiments, the taste-masking agent comprises peppermint oil and the texture agent comprises glycine.

In certain embodiments, the tablet comprises an active agent, a solubility enhancing carrier, porous particles, a binder, a modifier, a disintegrant, a taste-masking agent, a texture agent, and a lubricant, wherein the amount of active agent present in the tablet is about 0.5% to about 2.5%, the amount of solubility enhancing agent present in the tablet is about 5% to about 10%, the amount of porous particles present in the tablet is about 5% to about 15%, the amount of binder present in the tablet is about 2% to about 8%, the amount of modifier present in the tablet is about 55% to about 75%, the amount of disintegrant present in the tablet is about 2% to about 8%, the amount of taste-masking agent present in the tablet is about 0.5% to about 2%, the amount of texture agent present in the tablet is about 0.5% to about 5%, and the amount of lubricant in the tablet is about 0.1% to about 1%, wherein the percentages are based upon the final weight of the tablet. In certain related embodiments, the active agent comprises risperidone, the taste-masking agent comprises polyoxyethylenated 12-hydroxystearate, the porous particles comprise calcium hydrogen phosphate or magnesium aluminometasilicate, the binder comprises hydroxypropylcellulose, and the modifier comprises calcium sulfate anhydrous or potassium phosphate monobasic in combination with mannitol. In other related embodiments, the disintegrant comprises cross-linked sodium carboxylmethylcellulose and the lubricant comprises magnesium stearate. In still other related embodiments, the taste-masking agent comprises peppermint oil and the texture agent comprises glycine.

In certain embodiments, the tablet comprises an active agent, a binder, a modifier, a disintegrant, a taste-masking agent, a texture agent, and a lubricant, wherein the amount of active agent present in the tablet is about 0.5% to about 2.5%, the amount of binder present in the tablet is about 2% to about 8%, the amount of modifier present in the tablet is about 65% to about 85%, the amount of disintegrant present in the tablet is about 2% to about 8%, the amount of taste-masking agent present in the tablet is about 5% to about 12%, the amount of texture agent present in the tablet is about 0.5% to about 5%, and the amount of lubricant in the tablet is about 0.1% to about 1%, wherein the percentages are based upon the final weight of the tablet. In certain related embodiments, the active agent comprises risperidone, the taste-masking agent comprises a methacrylate polymer (e.g., dimethylaminoethyl methacrylate) and a meth-/acrylate polymer, the binder comprises hydroxypropylcellulose, and the modifier comprises calcium sulfate anhydrous or potassium phosphate monobasic in combination with mannitol. In other related embodiments, the disintegrant comprises cross-linked sodium carboxylmethylcellulose and the lubricant comprises magnesium stearate. In still other related embodiments, the taste-masking agent comprises peppermint oil and the texture agent comprises glycine.

In certain embodiments, the tablet comprises an active agent, porous particles, a binder, a modifier, a disintegrant, a taste-masking agent, a texture agent, and a lubricant, wherein the amount of active agent present in the tablet is about 0.5% to about 2.5%, the amount of porous particles in the tablet is about 5% to about 15%, the amount of binder present in the tablet is about 2% to about 8%, the amount of modifier present in the tablet is about 60% to about 75%, the amount of disintegrant present in the tablet is about 2% to about 8%, the amount of taste-masking agent present in the tablet is about 3% to about 9%, the amount of texture agent present in the tablet is about 0.5% to about 5%, and the amount of lubricant in the tablet is about 0.1% to about 1%, wherein the percentages are based upon the final weight of the tablet. In certain related embodiments, the active agent comprises risperidone, the taste-masking agent comprises hydroxypropylcellulose, the porous particles comprise calcium hydrogen phosphate or magnesium aluminometasilicate, the binder comprises hydroxypropylcellulose, and the modifier comprises calcium sulfate anhydrous or potassium phosphate monobasic in combination with mannitol. In other related embodiments, the disintegrant comprises cross-linked sodium carboxylmethylcellulose and the lubricant comprises magnesium stearate. In still other related embodiments, the taste-masking agent comprises peppermint oil and the texture agent comprises glycine.

In certain embodiments, the tablet comprises an active agent, porous particles, a binder, a modifier, a disintegrant, a taste-masking agent, a texture agent, and a lubricant, wherein the amount of active agent present in the tablet is about 0.5% to about 2.5%, the amount of porous particles in the tablet is about 5% to about 15%, the amount of binder present in the tablet is about 1% to about 6%, the amount of modifier present in the tablet is about 65% to about 80%, the amount of disintegrant present in the tablet is about 2% to about 8%, the amount of taste-masking agent present in the tablet is about 1% to about 6%, the amount of texture agent present in the tablet is about 0.5% to about 5%, and the amount of lubricant in the tablet is about 0.1% to about 1%, wherein the percentages are based upon the final weight of the tablet. In certain related embodiments, the active agent comprises risperidone, the taste-masking agent comprises polyvinylpyrrolidone, the porous particles comprise calcium hydrogen phosphate or magnesium aluminometasilicate, the binder comprises hydroxypropylcellulose, and the modifier comprises calcium sulfate anhydrous or potassium phosphate monobasic in combination with mannitol. In other related embodiments, the disintegrant comprises cross-linked sodium carboxylmethylcellulose and the lubricant comprises magnesium stearate. In still other related embodiments, the taste-masking agent comprises peppermint oil and the texture agent comprises glycine.

In another aspect, a method for manufacturing a tablet disclosed herein is provided. In certain embodiments, the method for manufacturing comprises: granulation of a binding agent (e.g., a binding agent comprising an LCST polymer) and a modifier (e.g., an LCST modifier) to produce a granulated mass; compression of the granulated mass to produce a tablet; and, optionally, color coating the tablet. In certain embodiments, the granulation process comprises wet granulation, fluid-bed granulation, roller-compaction granulation, or any combination thereof.

In another aspect, a container comprising a tablet disclosed herein is provided. In certain embodiments, the container comprises, or is accompanied by, an instruction. For example, in certain embodiments, the container is a bottle (e.g., a bottle used for dispensing pharmaceuticals). In other embodiments, the container is a package (e.g., a package comprising one or more wells, wherein the tablet is located in a well and a protective membrane covers the top of the well). In certain embodiments, the container comprises two or more tablets. In certain embodiments, the container is a package and the tablets are separated from one another (e.g., the tablets are in wells sized for individual tablets).

In certain embodiments, the instructions are attached to the container. In certain embodiments, the instructions provide that the tablet is for oral administration, that the tablet disintegrates or dissolves upon contact with saliva, that the active agent is predominantly absorbed in the buccal cavity, that the tablet reduces first pass metabolism of the active agent, that the tablet enhances bioavailability of the active agent, that the tablet reduces the time it takes for the active agent to achieve maximal effect, or any combination thereof.

In another aspect, a method of reducing first pass metabolism of an orally administered active agent in a subject is provided. As used herein, "first pass metabolism" refers to the enzymatic breakdown of an active agent as it passes through the gastrointestinal tract. In certain embodiments, the method comprises providing an orodispersable tablet disclosed herein to a subject, wherein the tablet includes the active agent. In certain embodiments, the tablet, when taken orally, disintegrates rapidly in the buccal cavity of the subject. In certain embodiments, the absorption of active agent occurs in the buccal cavity of the subject. For example, in certain embodiments, all of the active agent in absorbed in the buccal cavity. In other embodiments, all of the active agent is absorbed in the buccal cavity and laryngal cavity combined. In other embodiments, at least 25%, 50%, 60%, 70%, 80%, 90%, or more of the active agent is absorbed in the buccal cavity. In still other embodiments, at least 25%, 50%, 60%, 70%, 80%, 90%, or more of the active agent is absorbed in the buccal cavity and laryngal cavity combined.

In another aspect, a method of enhancing bioavailability of an active agent in a subject is provided. In certain embodiments, the method comprises providing an orodispersable tablet disclosed herein to a subject, wherein the tablet includes the active agent. The In certain embodiments, the tablet, when taken orally, disintegrates rapidly in the buccal cavity of the subject. In certain embodiments, the absorption of active agent occurs in the buccal cavity of the subject. For example, in certain embodiments, all of the active agent in absorbed in the buccal cavity. In other embodiments, all of the active agent is absorbed in the buccal cavity and laryngal cavity combined. In other embodiments, at least 25%, 50%, 60%, 70%, 80%, 90%, or more of the active agent is absorbed in the buccal cavity. In still other embodiments, at least 25%, 50%, 60%, 70%, 80%, 90%, or more of the active agent is absorbed in the buccal cavity and laryngal cavity combined.

In yet another aspect, a method of reducing the time for an active agent to achieve maximal effect in a subject is provided. In certain embodiments, the method comprises providing an orodispersable tablet disclosed herein to a subject, wherein the tablet includes the active agent. In certain embodiments, the tablet, when taken orally, disintegrates rapidly in the buccal cavity of the subject. In certain embodiments, the absorption of active agent occurs in the buccal cavity of the subject. For example, in certain embodiments, all of the active agent is absorbed in the buccal cavity. In other embodiments, all of the active agent is absorbed in the buccal cavity and laryngal cavity combined. In other embodiments, at least 25%, 50%, 60%, 70%, 80%, 90%, or more of the active agent is absorbed in the buccal cavity. In still other embodiments, at least 25%, 50%, 60%, 70%, 80%, 90%, or more of the active agent is absorbed in the buccal cavity and laryngal cavity combined.

The following examples illustrate aspects of the invention. The examples should, of course, be understood to be merely illustrative of only certain embodiments of the invention and not to constitute limitations upon the scope of the invention, which is defined by the claims that are appended at the end of this description.

EXAMPLES

Example 1

The critical solution temperature of a polymer can be measured by spectrophotometry, by differential scanning calorimetry, or by nuclear magnetic resonance spectroscopy. For example, the spectrophotometrical method can be used to measure the cloud point of an LCST polymer. "Cloud point" generally refers to the temperature where the polymer solution in an aqueous medium becomes cloudy, indicating initiation of precipitation or flocculation of the polymer. The spectrophotometical method, as described as follows, can be adopted to screen various combinations of LCST polymers and modifiers to determine whether a modifier is capable of reducing the LCST of a polymer to about 37° C. or lower.

Figure 1:
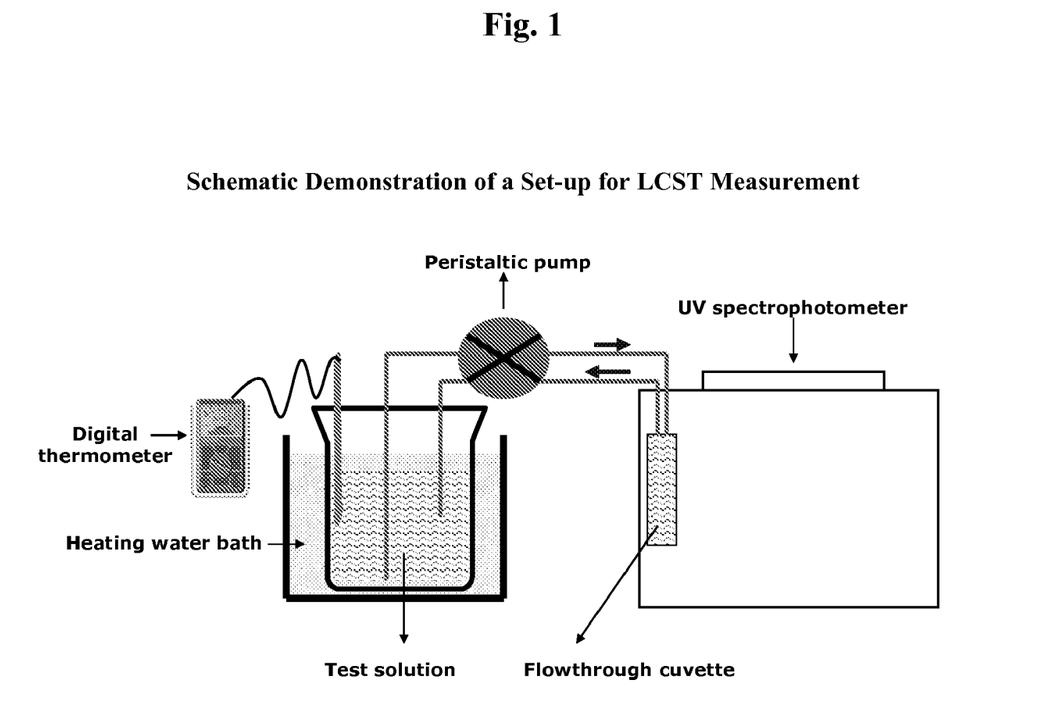
FIG. 1 is a schematic diagram showing one possible configuration of equipment that can be used to measure the LCST of a polymer.

An LCST polymer is dissolved in distilled water and, optionally, separate solutions of LCST modifiers at various concentrations. Each polymer or polymer/modifier test solution is placed in a separate container, such as a bottle or a beaker, and each container is placed in a water bath. The water bath is equipped with a temperature regulator, and the temperature of the bath is set at approximately 60° C. (the temperature of the bath can start at a high temperature or, alternatively, the temperature of the water bath can start low and be increased gradually at a rate of, e.g., 1° C./min). While in the water bath, each test solution is circulated through a 1-cm flowthrough quartz cuvette using a peristaltic pump (Masterflex) at a flow rate of 50 ml/min. The temperature of the test solution is monitored using a thermocouple, the lead of which is inserted into the test solution in the container. Alternatively, the lead of the thermocouple can be inserted into the cuvette through tubing connecting the container and the cuvette. The light transmission (T %) of each solution is measured spectrophotometrically with a UV spectrophotometer at a wavelength of 750 nm. Initially, spectrophotometric measurements are taken at 2-3° C. intervals. Near the cloud point of a particular polymer or polymer/modifier combination, spectrophotometric measurements are taken more frequently (e.g., at 1° C. intervals). The cloud point is ascertained as the temperature at which the light transmission is 90% of the transmission at room temperature. A schematic diagram of a set-up for LCST measurement is shown in FIG. 1.

Figure 2:
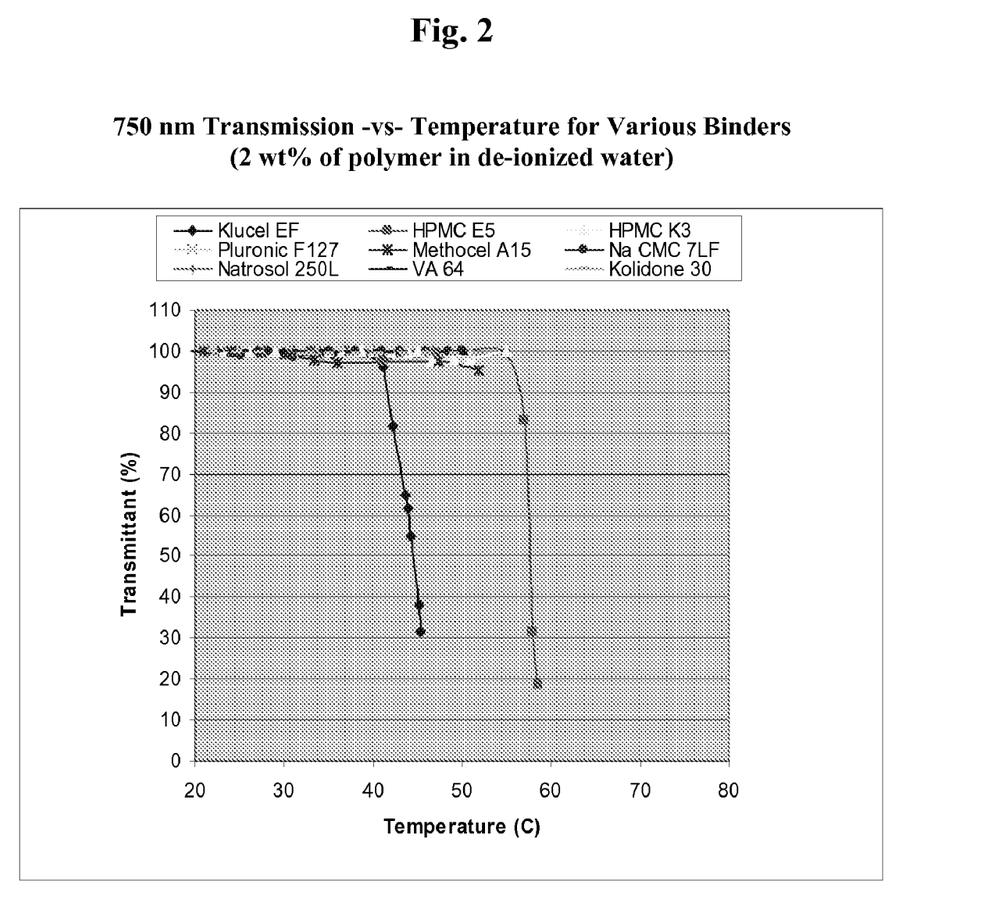

This spectrophotometrical method was used to study the LCST behavior of hydroxypropylcellulose (Klucel® EF), hydroxypropylmethylcellulose, Poly(oxyethylene-co-oxypropylene), methylcellulose, sodium carboxylmethylcellulose, hydroxyethylcellulose, poly(vinyl acetate-co-vinyl pyrrolidone, and Poly(vinyl pyrrolidone K29-32) in aqueous solution. The results for solutions containing 2 wt % of polymer in distilled water are shown in FIG. 2. The results indicate that, of the binding polymers tested, hydroxypropylcellulose had an LCST of about 42° C., the lowest of any of the polymers tested. The LCST for hydroxypropylmethylcellulose was around 56° C.

Figure 3:
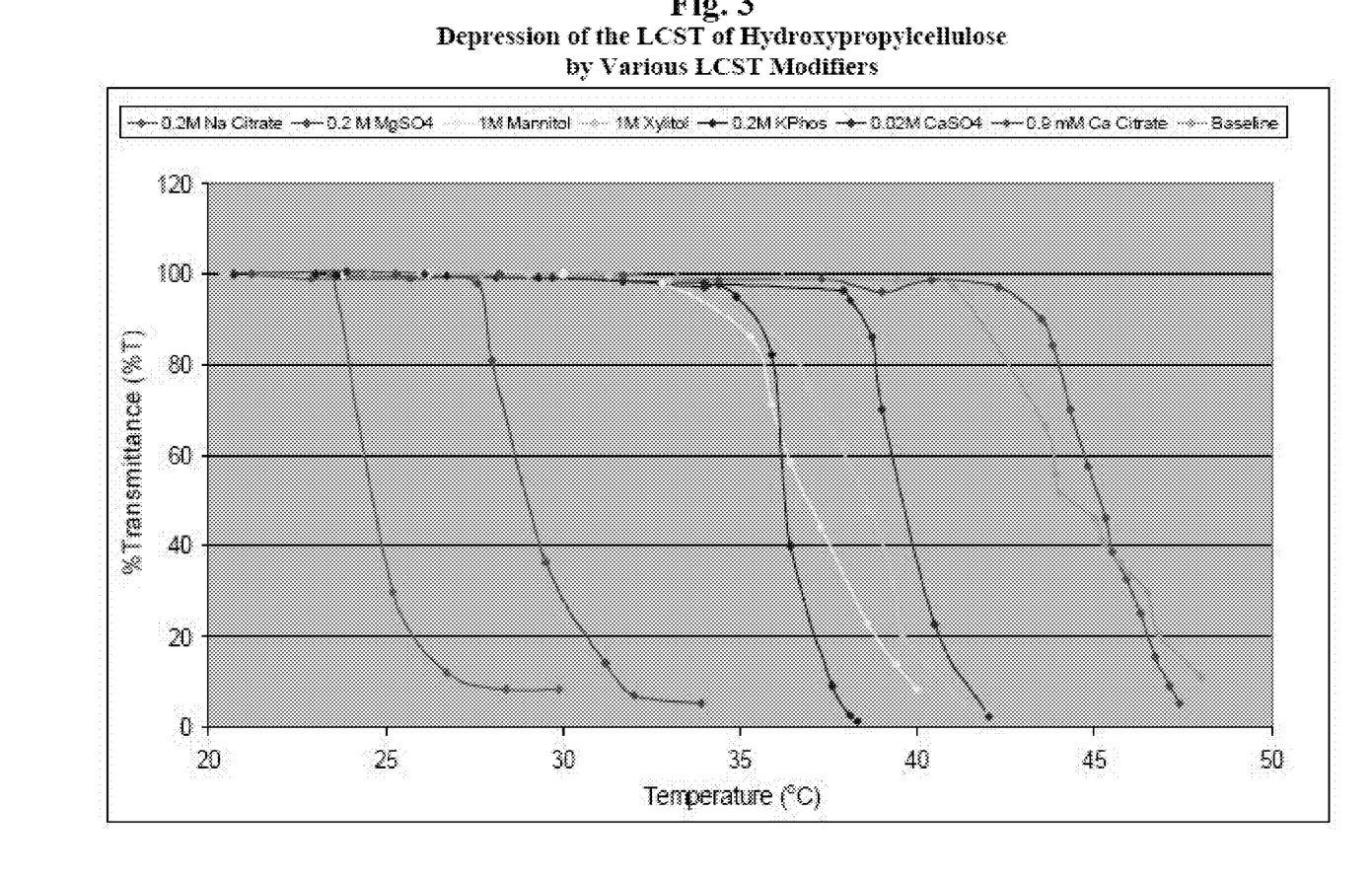
FIG. 3 is a graph showing percent transmission (T %) of 750 nm light through various solutions containing combinations of hydroxypropylcellulose (Klucel® EF) and a modifier as a function of temperature. Each solution contains 2 wt % hydroxypropylcellulose dissolved in deionized water (baseline), 0.2M sodium citrate, 0.2M magnesium sulfate, 1M mannitol, 1M xylitol, 0.2M potassium phosphate monobasic, 0.02M calcium sulfate, or 0.9mM calcium citrate. The graph shows that sodium citrate, magnesium sulfate, mannitol, xylitol, potassium phosphate monobasic, and calcium sulfate are all capable of reducing the LCST of hydroxypropylcellulose.
Figure 4:
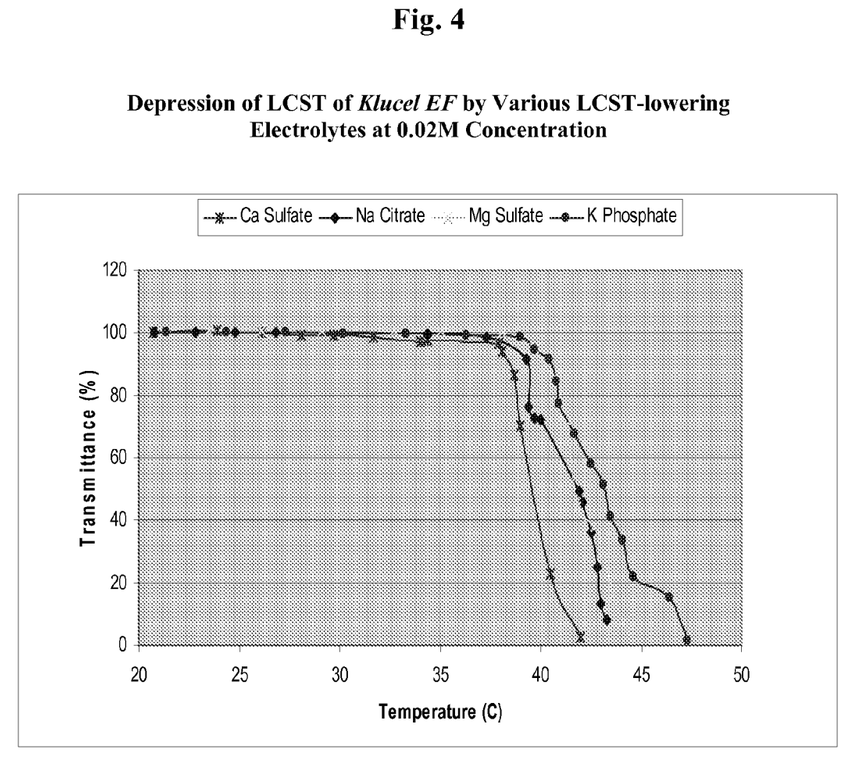
FIG. 4 is a graph showing percent transmission (T %) of 750 nm light through various solutions containing combinations of hydroxypropylcellulose (Klucel® EF) and an electrolyte modifier as a function of temperature. Each solution contains 2 wt % hydroxypropylcellulose dissolved in 0.02M sodium citrate, 0.02M magnesium sulfate, 0.02M potassium phosphate monobasic, or 0.02M calcium sulfate. The graph shows that, when compared at equivalent low concentrations, calcium sulfate has the strongest effect on reducing the LCST of hydroxypropyl-cellulose.

The effect of different modifiers on the LCST of hydroxypropylcellulose (Klucel® EF) is shown in FIG. 3. The results show that 0.2 M sodium citrate, 0.2M magnesium sulfate, 0.2M potassium phosphate (monobasic), 0.02M calcium sulfate, 1M mannitol and 1M xylitol each significantly reduce the LCST of hydroxypropylcellulose. With respect to reducing the LCST of hydroxypropylcellulose, the electrolytes tended to be more potent reducers than the saccharides tested. Among the electrolytes, calcium sulfate was the most effective reducer of hydroxypropylcellulose LCST when the electrolytes were present at a concentration of 0.02M. See FIG. 4.

Example 2

Figure 5:
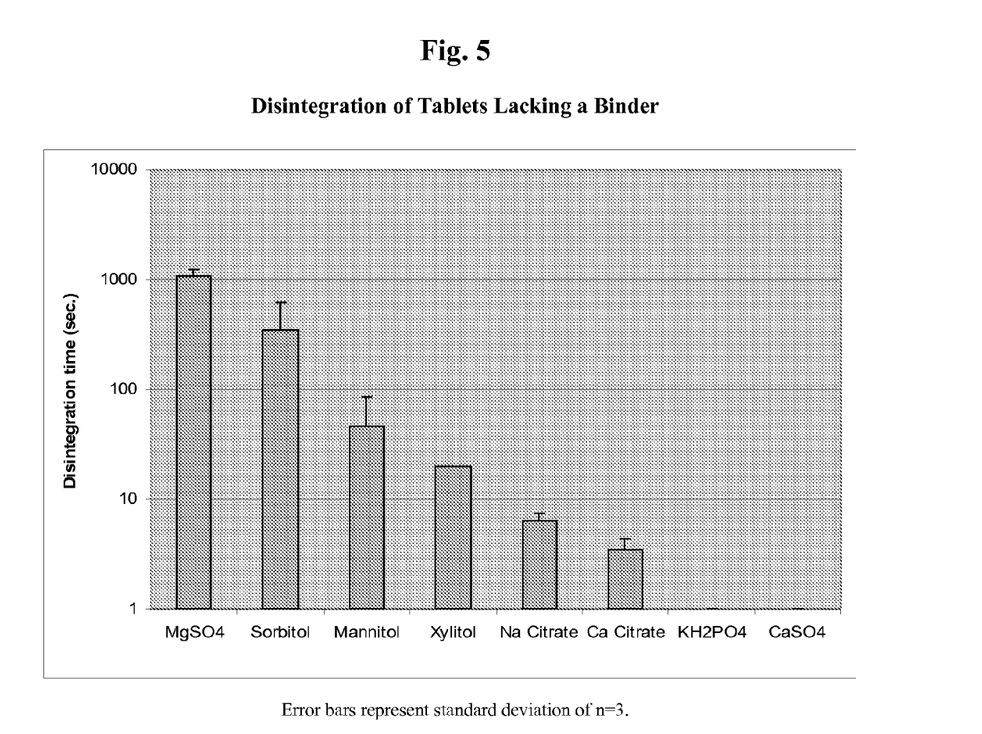
FIG. 5 is a graph showing the disintegration times for tablets containing 95 wt % of a particular modifier dry-blended with 5 wt % of crosslinked sodium carboxylmethylcellulose (Croscarmellose). For each modifier, three tablets (500 mg, 1.3 cm diameter, formed by compression under one metric ton) were tested for their rate of disintegration (shown in seconds) in deionized water at 37° C. During the disintegration process, the deionized water was agitated by means of a 200 rpm paddle. The graph shows the average disintegration rate and standard deviation (n=3).

To compare the cohesive properties of the modifiers tested in Example 2, tablets containing 95 wt % of each potential LSCT modifier and 5 wt % of cross-linked sodium carboxylmethylcellulose (Croscarmellose sodium) were tested for their average disintegration time in aqueous medium using a disintegration tester (LIJ-2, Vanguard Pharmaceutical Machinery, Inc. USA). See FIG. 5. The potential LCST modifier and Croscarmellose sodium were dry-blended in a vial and 500 mg of each blend were compressed under 1 metric ton of compression pressure using a 1.3 cm diameter rounding tool. The resulting tablets were placed into 300 ml of deionized (DI) water (at 37° C., agitated using a 200 rpm paddle) and the disintegration times of the tablets (i.e., the time that it took for each tablet to completely dissolve) were measured. Disintegration times were measured for three tablets of each modifier and average disintegration rates and standard deviates were determined. Under these conditions, tablets comprising calcium sulfate and potassium phosphate monobasic had the fastest disintegration times, each dissolving within about one second.

Example 3

An orally disintegrating placebo tablet comprising hydroxypropylcellulose as the LCST polymer and calcium sulfate as the modifier was manufactured as follows. 89.5 wt % calcium sulfate dihydrate, 5.0 wt % hydroxypropylcellulose (Klucel® EF), 5.0 wt % Croscarmellose sodium (Ac-di-Sol), and 0.5 wt % magnesium stearate were dry-blended on a roller mixer for approximately 1 hour. 500 mg of the dry-blend were compressed under 1 metric ton to a round tablet with diameter of 1.3 cm, using a Carver press. The mean disintegration time of the tablets (n=3) was 35 seconds, with standard deviation of 4 seconds, as measured in de-ionized water at 37° C. using a disintegration tester (LIJ-2, Vanguard Pharmaceutical Machinery, Inc. USA).

Example 4

An orally disintegrating placebo tablet comprising hydroxypropylcellulose as the LCST polymer and potassium phosphate monobasic as the modifier was manufactured according to the method of Example 3. The tablet formulation consisted of 89.5 wt % potassium phosphate monobasic, 5.0 wt % hydroxypropylcellulose (Klucel® EF), 5.0 wt % Croscarmellose sodium (Ac-di-Sol), and 0.5 wt % magnesium stearate. The mean disintegration time of the tablets was 36 seconds, with standard deviation of 4 seconds.

Example 5

An orally disintegrating placebo tablet comprising hydroxypropylcellulose as the LCST polymer and a combination of calcium sulfate and mannitol as the modifier was manufactured according to the method of Example 3, except that 200 mg of the placebo formulation were compressed into a round tablet with diameter of 5/16 inch (or 7.94 mm). The tablet formulation consisted of 45.0 wt % calcium sulfate dihydrate, 44.5 wt % mannitol, 5.0 wt % hydroxypropylcellulose (Klucel® EF), 5.0 wt % Croscarmellose sodium (Ac-di-Sol), and 0.5 wt % magnesium stearate.

Example 6

An orally disintegrating placebo tablet comprising hydroxypropylcellulose as the LCST polymer and a combination of potassium phosphate monobasic and mannitol as the modifier was manufactured according to the method of Example 5. The tablet formulation consisted of 45.0 wt % potassium phosphate monobasic, 44.5 wt % mannitol, 5.0 wt % hydroxypropylcellulose (Klucel® EF), 5.0 wt % Croscarmellose sodium (Ac-di-Sol), and 0.5 wt % magnesium stearate.

Example 7

An orally disintegrating placebo tablet comprising hydroxypropylcellulose as the LCST polymer, a combination of calcium sulfate and mannitol as the modifier, and a porous carrier was manufactured according to the method of Example 5. The tablet formulation consisted of 40.0 wt % calcium sulfate dihydrate, 39.5 wt % mannitol, 10.0 wt % calcium hydrogen phosphate particles (Fujicalin® SG), 5.0 wt % hydroxypropylcellulose (Klucel® EF), 5.0 wt % Croscarmellose sodium (Ac-di-Sol), and 0.5 wt % magnesium stearate.

Example 8

An orally disintegrating placebo tablet comprising hydroxypropylcellulose as the LCST polymer and a combination of potassium phosphate monobasic and mannitol as the modifier was manufactured according to the method of Example 5. The tablet formulation consisted of 40.0 wt % potassium phosphate monobasic, 39.5 wt % mannitol, 10.0 wt % calcium hydrogen phosphate particles (Fujicalin® SG), 5.0 wt % hydroxypropylcellulose (Klucel® EF), 5.0 wt % Croscarmellose sodium (Ac-di-Sol), and 0.5 wt % magnesium stearate.

Example 9

Tablets of the invention can be tested for friability using a standard test procedure. For example, the weight (W1) of a sample of 10 tablets is determined, after first de-dusting the tablets. The tablets are then placed into a test drum and allowed to rotate 100 times. Afterwards, accumulated dust is removed from the tablets and the tablets are re-weighed (W2). Friability is calculated as percent weight loss using the formula (W1−W2)/W1*100. If necessary, the test can be repeated, with the resulting weight loss calculated as the mean of the different test results.

The mechanical properties, including hardness and friability, of the tablets in Examples 5-8 were measured, using a tablet hardness tester (LIH-3, Vanguard Pharmaceutical Machinery, Inc. USA) and a friability tester (LIC-2, Vanguard Pharmaceutical Machinery, Inc. USA), respectively. The disintegration times of these tablets were also measured, as described in Example 2. The test results are shown in Table 1. All of the tablets tested exhibited both rapid disintegration times and desirable mechanical properties.

TABLE 1

Properties of Exemplary Orally Disintegrating Placebo Tablets

| Formulation | Disintegration time (sec) Mean (s.d) | Hardness (kg) Mean (s.d) | Friability (%) |
|---|---|---|---|
| Example 3 | 26.5 (5.0) | 4.10 (0.39) | 0.00 |
| Example 4 | 24.0 (3.0) | 1.76 (0.41) | 0.02 |
| Example 5 | 21.0 (2.8) | 4.57 (0.61) | 0.01 |
| Example 6 | 21.5 (2.1) | 2.93 (0.65) | 0.01 |

Example 10

An orally disintegrating tablet comprising risperidone, hydroxypropylcellulose as the LCST polymer, and a combination of calcium sulfate and mannitol as the modifier can be manufactured as follows. The formulation of this example consists of 2 wt % risperidone, 45.0 wt % calcium sulfate anhydrous, 38.5 wt % mannitol, 5.0 wt % hydroxypropylcellulose (Klucel® EF), 5.0 wt % Croscarmellose sodium (Ac-di-Sol), 1.0 wt % peppermint oil, 3.0 wt % glycine and 0.5 wt % magnesium stearate. All of the dry components are sieved individually through a 40-mesh screen. The sieved ingredients (except magnesium stearate) are then dry-blended in a V-blender for 10 minutes. The resulting dry blend is compacted using a roller compactor with a 1.25-mm screen. The compacted dry blend is then blended with 0.5% magnesium stearate and spearmint oil in the V-blender. Finally, 200 mg of the resulting granules are compressed into a round tablet with diameter of 5/16 inch (or 7.94 mm) on a tablet press.

Example 11

An orally disintegrating tablet comprising risperidone loaded into a porous particle carrier, hydroxypropylcellulose as the LCST polymer, and a combination of calcium sulfate and mannitol as the modifier can be manufactured as follows. The formulation of this example consists of 2 wt % risperidone, 8.0 wt % polyethylene glycol-modified 12-hydroxystearate (Solutol® HS-15), 10 wt % calcium hydrogen phosphate particles (Fujicalin® SG), 35.0 wt % calcium sulfate anhydrous, 30.5 wt % mannitol, 5.0 wt % hydroxypropylcellulose (Klucel® EF), 5.0 wt % Croscamellose sodium (Ac-di-Sol), 1.0 wt % peppermint oil, 3.0 wt % glycine and 0.5 wt % magnesium stearate. Risperidone and Solutol SH-15 are first dissolved in a minimum amount of methyl ethyl ketone (MEK) at an elevated temperature (e.g., using a ratio of approximately 2:8:10 (wt/wt/vol) of rispseridone:Solutol:MEK). The solution is then absorbed/adsorbed into the porous Fujicalin® SG carrier. Next, the MEK is evaporated from the solution-sorbing carrier. The adsorbed porous particles and the rest of the excipients are dry-blended, granulated, and compressed into tablets, as described in Example 10, with the adsorbed porous particles mixed in at either the first or second dry blending step.

Example 12

An orally disintegrating tablet comprising encapsulated risperidone, hydroxypropylcellulose as the LCST polymer, and a combination of calcium sulfate and mannitol as the modifier can be manufactured as follows. The formulation of this example consists of 2 wt % risperidone, 8.0 wt % dimethylaminoethyl methacrylate: meth-/acrylate polymer (Eudragit® 100/Eudragit® NE, 9:1 by wt), 40.0 wt % calcium sulfate anhydrous, 35.5 wt % mannitol, 5.0 wt % hydroxylpropylcellulose (Klucel® EF), 5.0 wt % Croscamellose sodium (Ac-di-Sol), 1.0 wt % peppermint oil, 3.0 wt % glycine and 0.5 wt % magnesium stearate. Risperidone and Eudragit® 100/Eudragit® NE are first dissolved in a minimum amount of ethanol. The resulting solution is spray-dried to encapsulate the drug. The encapsulated drug and the rest of the excipients are dry-blended, granulated, and compressed into tablets, as described in Example 10.

Example 13

An orally disintegrating tablet comprising risperidone loaded into a porous particle carrier, hydroxypropylcellulose as the LCST polymer, and a combination of calcium sulfate and mannitol as the modifier can be manufactured as follows. The formulation of this example consists of 2 wt % risperidone, 35.0 wt % calcium sulfate anhydrous, 33.5 wt % mannitol, 10 wt % calcium hydrogen phosphate particles (Fujicalin® SG), 10.0 wt % hydroxypropylcellulose (Klucel® EF), 5.0 wt % Croscamellose sodium (Ac-di-Sol), 1.0 wt % peppermint oil, 3.0 wt % glycine and 0.5 wt % magnesium stearate. Risperidone and a half of the Klucel® EF are first dissolved in a minimum amount of ethanol or MEK. The resulting solution is absorbed into the porous carrier Fujicalin SG and the ethanol or MEK is evaporated from the solution-sorbing carrier. The adsorbed porous particles and the rest of the excipients are dry-blended, granulated, and compressed into tablets, as described in Example 10, with the adsorbed porous particles mixed in at either the first or second dry blending step.

Example 14

An orally disintegrating tablet comprising risperidone loaded into a porous particle carrier, hydroxypropylcellulose as the LCST polymer, and a combination of calcium sulfate and mannitol as the modifier can be manufactured as follows. The formulation of this example consists of 2 wt % risperidone, 38.0 wt % calcium sulfate anhydrous, 35.5 wt % mannitol, 10 wt % calcium hydrogen phosphate particles (Fujicalin® SG), 3.0 wt % hydroxypropylcellulose (Klucel® EF), 2.0 wt % polyvinylpyrrolindone (PVP k12), 5.0 wt % Croscamellose sodium (Ac-di-Sol), 1.0 wt % peppermint oil, 3.0 wt % glycine and 0.5 wt % magnesium stearate. Risperidone and polyvinylpyrrolidone (PVP k12) are first dissolved in a minimum amount of ethanol or MEK. The resulting solution is absorbed into the porous carrier Fujicalin SG and the ethanol or MEK is evaporated from the solution-sorbing carrier. The adsorbed porous particles and the rest of the excipients are dry-blended, granulated, and compressed into tablets, as described in Example 10, with the adsorbed porous particles mixed in at either the first or second dry blending step.

Example 15

Each of the orally disintegrating tablets of Examples 10 through 13 can be formulated using potassium phosphate monobasic in place of calcium sulfate.

Example 16

Active pharmaceutical ingredients (API) other than risperidone can be incorporated into the fast disintegrating and fast dissolving tablets of the invention. Such alternative APIs include amphentamine/dextroamphentamine, dextromethorphan, donepezil HCl, ergotamine tartrate, fentanyl, granisetron HCl, methylphenidate HCl, ondansetron, ramosetron HCl, risperidone, sufentanil, sumatriptan succinate, zaleplon, zolpidem tartrate, and zopiclone. With appropriate adjustments for API dosage, each of these APIs can be incorporated into a orally disintegrating tablet of Examples 10 through 13.

Example 17

Other granulation methods, such as wet-granulation and fluid-bed granulation can be used to prepare the granules of the compositions revealed in Examples 10-13.

Thus, for example, LCST polymer/modifier combinations (e.g., as disclosed herein) can be mixed and formed into a tablet as follows. The modifier and LCST polymer are first combined in a weight ratio of about 20:1 to about 1:2, depending upon the particular combination. An LSCT polymer/modifier combination is then passed through a 30-mesh screen and homogeneously dry-blended in a mixer. The dry blend is wet-granulated using anhydrous ethanol as a granulating solvent until a consistent wet mass is obtained. Next, the wet mass is passed through a 20-mesh screen and dried at room temperature overnight. Afterwards, the dried granules are passed through a 16-mesh screen. The dried and screened granules are blended, for example, with 0.5% magnesium stearate. The resulting granules are compressed into tablets using, for example, a Carver press and a round punch (e.g., a round punch having a 10 mm diameter). The target weight of each tablet can be about 200 mgs. The resulting tablet can be assessed for its disintegration time, as well as its mechanical properties, such as hardness and friability.

Example 18

Tablet formulations comprising a carrier for the active agent can be prepared as follows. First, a micelle formulation is prepared. A poorly water-soluble drug is first dissolved in a non-ionic surfactant, such as polyoxyl castor oil (e.g., Cremophor EL®), polysorbate 80 (Tween 80®), vitamin E TPGS, or any mixture thereof. The drug content of the solution can be in the range of 0.1 to 10% by weight. Next, the drug solution is admixed with a plurality of porous particles, such as calcium hydrogen phosphate particles or magnesium aluminometasilicate particles (e.g., Fujicalin® or Neusilin™, respectively), at a weight ratio of drug solution to particles varying from about 1:20 to 2:1, and the drug solution is allowed to sorb into the pores of the porous particles. The liquid-sorbing particles are then blended with other excipients and processed as described in Example 16.

Example 19

The procedure in Example 17 can be repeated using a self-emulsifying formulation (SEF) instead of a micelle formulation. The self-emulsifying drug solution can be composed of 1.0% hydrophobic drug, 49.5% non-ionic surfactant (e.g., polyoxyl castor oil, such as Cremophor EL®), and 49.5% distilled acetylated monoglyceride (e.g., Myvacet™ 9-45), by weight.

Example 20

The procedure in Example 17 can be repeated using an alternative SEF instead of a micelle formulation. The alternative self-emulsifying drug solution can be composed of 1.0% hydrophobic drug, 49.5% non-ionic surfactant (e.g., vitamin E TPGS), and 49.5% oil (e.g., vitamin E), by weight.

Example 21

The procedure in Example 17 can be repeated using yet another SEF instead of a micelle formulation. The alternative self-emulsifying drug solution of this example can be composed of 2.50% hydrophobic drug, 48.75% non-ionic surfactant (e.g., vitamin E TPGS), and 48.75% oil (e.g., vitamin E), by weight.

Particular features of the invention are emphasized in the claims which follow.

What is claimed:
1. An orodispersable tablet comprising:
   an active agent;
   a binder comprising a polymer which is hydroxypropylcellulose or hydroxypropylmethylcellulose having a lower critical solution temperature (LCST) greater than 40° C.; and
   a modifier,
   wherein the ratio of modifier to said polymer is 30:1 to 2:1;
   wherein said modifier reduces the LCST of said polymer to 37° C. or less; and
   wherein in the absence of a disintegrant the tablet disintegrates in less than 60 seconds when administered orally.
2. The tablet of claim 1, wherein said modifier is an electrolyte, and wherein said electrolyte comprises a cation selected from the group consisting of calcium, magnesium, potassium, sodium, or a combination thereof.

3. The tablet of claim 1, wherein said modifier is an electrolyte, and wherein said electrolyte comprises an anion selected from the group consisting of citrate, phosphate, sulfate, or a combination thereof.

4. The tablet of claim 1, wherein the modifier is an electrolyte selected from the group consisting of calcium sulfate, magnesium sulfate, potassium phosphate, and sodium citrate.

5. The tablet of claim 1, wherein the modifier is a polyol selected from the group consisting of mannitol and xylitol.

6. The tablet of claim 1, wherein the modifier comprises an electrolyte selected from the group consisting of calcium sulfate, magnesium sulfate, potassium phosphate, and sodium citrate, and a polyol selected from the group consisting of mannitol and xylitol.

7. The tablet of claim 1, wherein the active agent is substantially insoluble in water.

8. The tablet of claim 1, wherein the active agent is a therapeutic agent selected from the group consisting of amphentamine/dextroamphentamine, dextromethorphan, donepezil HCl, ergotamine tartrate, fentanyl, fentanyl citrate, granisetron HCl, methylphenidate HCl, ondansetron, ramosetron HCl, risperidone, sufentanil, sufentanil citrate, sumatriptan succinate, zaleplon, zolpidem tartrate, and zopiclone.

9. The tablet of claim 1, wherein the active agent is risperidone.

10. The tablet of claim 1, wherein said tablet has a friability less than 2%.

11. The tablet of claim 1, further comprising a carrier for the active agent, wherein the carrier comprises porous particles, a solubility enhancing agent, a taste-masking agent, a temperature responsive agent, or a combination thereof.

12. The tablet of claim 1, further comprising a lubricant, a taste-masking agent, a bulking agent, or any combination thereof.

13. A method for manufacturing a tablet of claim 1, comprising:
granulating said polymer and said modifier to produce a granulated mass;
compressing said granulated mass to produce a tablet; and
optionally, color coating said tablet.

14. The method of claim 13, wherein said granulating comprises wet granulation, fluid-bed granulation, roller-compaction granulation, or a mixture thereof.

15. A container comprising a tablet of claim 1 and an instruction, wherein said instruction provides:
the tablet is to be taken orally; and
the tablet disintegrates upon contact with saliva in less than 60 seconds.

16. The container of claim 15, wherein said instruction further provides that active agent is absorbed in the buccal cavity, the tablet reduces first pass metabolism of the active agent, the tablet enhances bioavailability of said active agent, the tablet reduces the time it takes for the active agent to achieve maximal effect, or any combination thereof.

17. A method of administering an active agent to a subject, the method comprising providing a tablet of claim 1 to said subject with instructions to take the tablet orally, wherein said tablet comprises said active agent.

18. The method of claim 17, wherein taking said tablet orally reduces first pass metabolism of said active agent in said subject, enhances bioavailability of said active agent in said subject, or reduces the time for said active agent to achieve maximal effect in said subject.

19. The method of claim 17, wherein taking said tablet orally results in absorption of said active agent in the buccal cavity of said subject.

20. The method of claim 17, wherein taking said tablet orally results in absorption of at least 50% of said active agent in said tablet in the buccal cavity of said subject.

* * * * *